(12) United States Patent
Liu et al.

(10) Patent No.: US 11,518,990 B2
(45) Date of Patent: Dec. 6, 2022

(54) IMMOBILIZED CYCLOALIPHATIC PEPTIDE ACYLTRANSFERASE AND PREPARATION METHOD AND USES THEREOF

(71) Applicant: SHANGHAI TECHWELL BIOPHARMACEUTICAL CO., LTD, Shanghai (CN)

(72) Inventors: Shidong Liu, Shanghai (CN); Zhaoli Zhang, Shanghai (CN); Xiaoming Ji, Shanghai (CN)

(73) Assignee: SHANGHAI TECHWELL BIOPHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 16/741,460

(22) Filed: Jan. 13, 2020

(65) Prior Publication Data

US 2020/0149029 A1    May 14, 2020

Related U.S. Application Data

(62) Division of application No. 14/400,473, filed as application No. PCT/CN2013/075508 on May 10, 2013, now abandoned.

(30) Foreign Application Priority Data

May 11, 2012 (CN) .......................... 201210148392.7

(51) Int. Cl.

| C12N 11/14 | (2006.01) |
|---|---|
| C12P 21/02 | (2006.01) |
| C12N 9/80 | (2006.01) |
| C07K 7/56 | (2006.01) |
| C12N 11/087 | (2020.01) |
| C12N 9/86 | (2006.01) |

(52) U.S. Cl.
CPC ................. *C12N 11/14* (2013.01); *C07K 7/56* (2013.01); *C12N 9/80* (2013.01); *C12N 9/86* (2013.01); *C12N 11/087* (2020.01); *C12P 21/02* (2013.01)

(58) Field of Classification Search
CPC .......... C07K 7/56; C12N 11/14; C12N 11/08; C12N 9/80; C12N 9/86; C12P 21/02; Y10S 435/815
See application file for complete search history.

(56) References Cited

U.S. PATENT DOCUMENTS

| 3,892,580 A | 7/1975 | Messing |
|---|---|---|
| 3,930,951 A | 1/1976 | Messing |
| 5,055,429 A | 10/1991 | James et al. |
| 5,376,634 A | 12/1994 | Iwamoto et al. |
| 2008/0182307 A1* | 7/2008 | Ben-Bassat ............... C12P 7/22 435/156 |

FOREIGN PATENT DOCUMENTS

| CN | 1161462 C | 8/2004 |
|---|---|---|
| CN | 102443050 A | 5/2012 |
| EP | 1934342 A1 | 6/2008 |
| EP | 2592140 A1 | 5/2013 |
| WO | 2007/036235 | 4/2007 |

OTHER PUBLICATIONS

Ueda et al. J. Antibiotics (2010) 63: 65-70 (Year: 2010).*
Ueda et al. J. Antibiotics (2011) 64: 169-175 (Year: 2011).*
Lumor et al. J. Agric. Food Chem. (2008) 56 10396-10398 (Year: 2008).*
Machine translation of CN 102747066A; published Oct. 24, 2012; priority to Jul. 31, 2012) from IP.com on Nov. 24, 2021 (Year: 2012).*
International Search Report for PCT/CN2013/075508, dated Jul. 29, 2013 (8 pages).
D. Hormigo et al., "Immobilized aculeacin A acylase from Actinoplanes utahensis: Characterization of a novel biocatalyst," Bioresource Technology, vol. 101 (2010), p. 4261-4268.
J. Torres-Bacete et al., "Newly Discovered Pencillin Acylase Activity of Aculeacin A Acylase from Actinoplanes utahensis," Applied and Environmental Microbiology, vol. 73, No. 16 (2007), p. 5378-5381.
Extended European Search Report; European Patent Application No. 13788659.4, dated Oct. 21, 2015 (6 pages).
Takeshima et al. J. Biochem. (1989) 105:606-610.
Torres-Bacete et al. Appl. Environ. Microbiol. (2007) 73(16): 5378-5381 (Year: 2007).
Seetharam et al. Enzyme Microb. Technol. (2002) 31: 747-753 (Year: 2002).
Ueda et al. J. Antibiotics (2011) 64: 169-175; published on line Dec. 1, 2010 (Year: 2010).
He et al. J. Molec. Catal. B: Enzymes (2000) 11: 45-53 (Year: 2000).

* cited by examiner

Primary Examiner — Susan M Hanley
(74) Attorney, Agent, or Firm — Hamre, Schumann, Mueller & Larson, P.C.

(57) ABSTRACT

Disclosed in the present invention are an immobilized cycloaliphatic peptide acyltransferase and a preparation method and use thereof. The cycloaliphatic peptide acyltransferase is immobilized on a carrier; the cycloaliphatic peptide acyltransferase is derived from natural or artificial mutants or variants thereof, or can be obtained by introducing a foreign cyclic acyltransferase gene and transforming thereafter; the material of the carrier is selected from an inorganic carrier or a polypropylene resin carrier. Also disclosed in the present invention are the preparation method for the immobilized cycloaliphatic peptide acyltransferase and uses thereof.

8 Claims, 1 Drawing Sheet

IMMOBILIZED CYCLOALIPHATIC PEPTIDE ACYLTRANSFERASE AND PREPARATION METHOD AND USES THEREOF

TECHNICAL FIELD

The present invention relates to enzyme immobilization, particularly to an immobilized cycloaliphatic peptide acyltransferase and preparation method and uses thereof.

BACKGROUND

Echinocandins, as a new class of antifungal agents, exhibit good effects in the treatment of infections caused by *Candida* or *Aspergillus*. Caspofungin, Micafungin and Anidulafungin are the representatives of such medicaments. Echinocandins inhibit fungus by suppressing the formation of 1,3-β glycosidic bond, so as to reduce the harm to human body, and reduce the side effects while remaining high efficiency. Therefore, they are safer in use than traditional antifungal agents.

FK463 (Micafungin) is the compound of formula [Ie], which is obtained by cutting the side-chain of FR901379 as precursor (compound of Formula Ia), thus forming FR179642 (compound of Formula [Ic]), and then by synthesis method.

Anidulafungin is the compound of formula [If], which is obtained by cutting the side-chain of echinocandin B as precursor (compound of Formula Ib), thus forming compound of Formula [Id], and then by synthesis method.

It has been reported that enzymes deacetylating the side-chain of cycloaliphatic peptides, such as FR901379, echinocandin B, Ciclosporin A and the like, belong to the enzymes produced by *Actinoplanes utahensis* IFO-13244, *A. utahensis* NRRL-12052. In WO97/32975, enzymes produced by bacteria belonging to *Streptomyces* (*Streptomyces anulatus* 4811 strain, *Streptomyces anulatus* 8703 strain, *Streptomyces* sp. 6907 strain) have been reported. Additionally, in WO97/47738, enzymes produced by *Oidiodendron tenuissimum* IFO 6797 strain, *Oidiodendron echinulatum* IFO 31963 strain, *Oidiodendron truncatum* IFO 9951 strain, *Oidiodendron truncatum* IFO 31812 strain, *Oidiodendron* sp. 30084 strain, *Verticillium* sp. 30085 strain have been reported.

The acyltransferase can be found in the cultured mycelium and filtrate. Generally, the bioactive substance can be recovered by the following process: the cultured broth is filtrated or centrifuged, so as to obtain mycelium and filtrate, and the obtained mycelium and filtrate are separated and purified by conventional methods, such as high concentration salt solution extraction, conventional solvent extraction, concentration under reduced pressure, lyophilization, pH adjustment, anion exchange resin or cation exchange resin, crystallization, recrystallization and the like, thereby obtaining the acyltransferase. In CN 1161462C, a deacylation method using the enzyme has been disclosed, wherein culture was used to transform cycloaliphatic peptides, such as FR901379, echinocandin B and the like. However, the drawback of the method is that there is organic solvent present in the transformation system, it is difficult to post-treat the product, conversion speed is low, acyltransferase can not be reused, and the purity of conversion product is low, thus increasing the difficulty to purify the deacylated product.

Therefore, people try to look for a method for fixing the enzyme, so as to recover, and purify the acyltransferase, and improve the utilization ratio of the enzyme.

SUMMARY OF THE INVENTION

One object of the present invention is to provide an immobilized cycloaliphatic peptide acyltransferase.

In the present invention, a preparation method for the immobilized cycloaliphatic peptide acyltransferase is also provided.

A further object of the present invention is to provide use of such immobilized cycloaliphatic peptide acyltransferase.

In the first aspect of the present invention, an immobilized cycloaliphatic peptide acyltransferase is provided. The cycloaliphatic peptide acyltransferase is immobilized on a carrier; said cycloaliphatic peptide acyltransferase is derived from natural or artificial mutants, or variants thereof and can be obtained through transformation by introducing foreign genes of cycloaliphatic peptide acyltransferase; and the carrier is selected from inorganic carrier, or porous, hydrophilic enzyme carrier.

The immobilized cycloaliphatic peptide acyltransferase is used to catalyze deacylation of acyl of $R^1$ in the compound of formula I, thereby obtaining the compound of formula II,

I

Wherein $R^1$ is an acyl, $R^2$ is a hydroxy or acyloxy, $R^3$ is a hydrogen or hydroxy, $R^4$ is a hydrogen or hydroxy, $R^5$ is a hydrogen or a hydroxy sulfonyloxy, and $R^6$ is a hydrogen or carbamoyl.

In a preferred embodiment, the compound or a pharmaceutically acceptable salt thereof which can be deacylated through catalysis is represented by formula Ia or Ib:

-continued

In a preferred embodiment, the carrier is selected from the following inorganic carrier: an inorganic carrier, wherein, based on the total weight of the inorganic carrier, the content of $SiO_2$ is more than 50 wt %, and the content of $Al_2O_3$ is more than 1 wt %; preferably, the inorganic carrier selected from: catalyst carrier CELITE, Expanded perlite, diatomaceous earth, kaolin, or porous glass.

In another preferred embodiment, the carrier is selected from the following porous hydrophilic enzyme-carrier: a porous hydrophilic enzyme-carrier in which polymethacrylate is used as matrix with bonded epoxide or containing amino functional groups; preferably selected from: Relizyme EP403, SEPABEADS EC-EP, Relizyme HA403 or SEPABEADS EC-HA.

In a preferred embodiment, in the immobilized cycloaliphatic peptide acyltransferase, 10-1000 unites (u), preferably 20-600 units (u) of cycloaliphatic peptide acyltransferase is immobilized on one gram of the carrier.

In another preferred embodiment, the immobilized cycloaliphatic peptide acyltransferase is immobilized on an inorganic carrier, and 10-100 unites (u), preferably 20-80 units (u) of cycloaliphatic peptide acyltransferase is immobilized on one gram of the carrier.

In another preferred embodiment, the immobilized cycloaliphatic peptide acyltransferase is immobilized on a porous hydrophilic enzyme-carrier, for example, an enzyme-carrier in which polymethacrylate is used as matrix with bonded epoxide or containing amino functional groups, and 100-1000 unites (u), preferably 120-600 units (u) of cycloaliphatic peptide acyltransferase is immobilized on one gram of the carrier.

In the second aspect of the present invention, a method for preparing the immobilized cycloaliphatic peptide acyltransferase of the present invention is provided, comprising the following steps:

mixing a solution containing free cycloaliphatic peptide acyltransferase with a carrier for adsorption and immobilization to obtain the immobilized cycloaliphatic peptide acyltransferase provided by the present invention as said above.

In the above preparation method, said cycloaliphatic peptide acyltransferase is derived from natural or artificial mutants, or variants and can be obtained through transformation by introducing foreign genes of cycloaliphatic peptide acyltransferase.

In the above preparation method, the strain is from *Actinoplanes* or *Streptomyces*.

In the above preparation method, the solution containing free cycloaliphatic peptide acyltransferase is obtained from the following manner: culturing the strain, so as to obtain the solution containing free cycloaliphatic peptide acyltransferase; or culturing the strain, and then breaking the cell wall of obtained hyphae, so as to obtain the solution containing free cycloaliphatic peptide acyltransferase; or purifying the solution containing free cycloaliphatic peptide acyltransferase and removing impurity protein, so as to obtain the pure solution containing free cycloaliphatic peptide acyltransferase.

In the above preparation method, the carrier is selected from inorganic carriers, or porous, hydrophilic enzyme carriers.

In the above preparation method, the carrier is selected from the following inorganic carrier: an inorganic carrier, wherein, based on the total weight of the inorganic carrier, the content of $SiO_2$ is more than 50 wt %, and the content of $Al_2O_3$ is more than 1 wt %; preferably, the inorganic carrier selected from: catalyst carrier CELITE, Expanded perlite, diatomaceous earth, kaolin, or porous glass.

In the above preparation method, the porous hydrophilic enzyme carrier is selected from the enzyme-carrier in which polymethacrylate is used as matrix with bonded epoxide or containing amino functional groups; preferably selected from: Relizyme EP403, SEPABEADS EC-EP, Relizyme HA403 or SEPABEADS EC-HA.

In the above preparation method, the mixing ratio of the free cycloaliphatic peptide acyltransferase to the carrier is 10-1000 unites (u), preferably 20-600 units (u) of enzyme vs one gram of carrier.

In the above preparation method, the mixing ratio of the free cycloaliphatic peptide acyltransferase to the inorganic carrier is 10-100 unites (u), preferably 20-80 units (u) of enzyme vs one gram of carrier.

In the above preparation method, the mixing ratio of the free cycloaliphatic peptide acyltransferase to the porous hydrophilic enzyme carrier is 100-1000 unites (u), preferably 120-600 units (u) of enzyme vs one gram of carrier.

In the above preparation method, the pH value of the solution containing free cycloaliphatic peptide acyltransferase is 4-9; preferably, 6-7.

In the above preparation method, the temperature for mixing the solution containing free cycloaliphatic peptide acyltransferase with the carrier is 0-80° C.; preferably, 20-35° C.; most preferably, 20-25° C.

In the above preparation method, after mixing the solution containing free cycloaliphatic peptide acyltransferase with the carrier, the free cycloaliphatic peptide acyltransferase is separated from the cycloaliphatic peptide acyltransferase binding to the carrier, so as to obtain the immobilized cycloaliphatic peptide acyltransferase.

In the third aspect of the present invention, a method for preparing the compound of formula II is provided, comprising the following steps:

(a) mixing the compound of formula I with a buffer solution, so as to obtain solution 1;

(b) mixing solution 1 with the immobilized cycloaliphatic peptide acyltransferase as said above provided by the present invention for conducting deacylation reaction, so as to give the compound of formula II;

Wherein $R^1$ is an acyl, $R^2$ is a hydroxy or acyloxy, $R^3$ is a hydrogen or hydroxy, $R^4$ is a hydrogen or hydroxy, $R^5$ is a hydrogen or a hydroxy sulfonyloxy, and $R^6$ is a hydrogen or carbamoyl.

In another preferred embodiment, the ratio of the immobilized cycloaliphatic peptide acyltransferase to the compound of formula I is 0.01-10 u/g.

In another preferred embodiment, the pH value of the buffer in step (a) is 4-9, preferably 6-7; and the buffer in step (a) is selected from one or more of the group consisting of sodium citrate buffer, potassium dihydrogen phosphate-disodium hydrogen phosphate buffer and Tris-HCl buffer.

In another preferred embodiment, the temperature for deacylation reaction in step (b) is 20-70° C.; preferably 40-50° C.

In another preferred embodiment, in step (b), upon deacylation, the immobilized cycloaliphatic peptide acyltransferase is separated from the product-containing reaction solution to give the compound of formula II; preferably, the method for separating the immobilized cycloaliphatic peptide acyltransferase from the product-containing reaction solution includes filtration or centrifugation.

Accordingly, a method for immobilizing cycloaliphatic peptide acyltransferase is provided, thereby recovering, purifying the acyltransferase, and improving the utilization of the enzyme.

MODE FOR CARRYING OUT THE INVENTION

After extensive researches, the inventors found an industrialized production method for immobilized cycloaliphatic peptide acyltransferase and a production method for deacylating the "amide group" on the side chain of cycloaliphatic peptides by using the immobilized enzyme preparations to form "amino group". The method is advanced, simple, and easy to operate, and the deacylated product will possess high purity.

Moreover, the present invention relates to the immobilization method for acyltransferase for deacylating the acyl side chain of FR901379 (Patent No. CN 1051757A) produced by *Colephoma* sp. F-11899 (FERM BP-2635), echinocandin B (U.S. Pat. No. 4,288,549) produced by *Aspergillus nidulans* Nrrl 11440 and the like, and the deacylation method by using the immobilized enzyme.

Structural formulae of compounds mentioned in BACKGROUND and the present invention are listed in the following table:

I

II (FR901379)

(echinocandin B)

-continued

(FR179642)

Ic

Id

-continued (FK463(Sodium Micafungin))

(Anidulafungin)

wherein $R^1$ is an acyl, $R^2$ is a hydroxy or acyloxy, $R^3$ is a hydrogen or hydroxy, $R^4$ is a hydrogen or hydroxy, $R^5$ is a hydrogen or a hydroxy sulfonyloxy, and $R^6$ is a hydrogen or carbamoyl.

The cycloaliphatic peptide acyltransferase according to the present invention is immobilized, and the preparation method thereof includes the following steps:

a. preparing a cycloaliphatic peptide acyltransferase liquid;

b. mixing the cycloaliphatic peptide acyltransferase liquid with a carrier based on certain ratio, so as to immobilize the cycloaliphatic peptide acyltransferase on the carrier; and c. separating the cycloaliphatic peptide acyltransferase liquid from the carrier, so as to obtain the immobilized cycloaliphatic peptide acyltransferase.

It is not necessary to define the source of cycloaliphatic peptide acyltransferase used in the present invention, and the cycloaliphatic peptide acyltransferase derived from natural or artificial mutants, or variants thereof and obtained through transformation by introducing foreign genes of cycloaliphatic peptide acyltransferase can be included in the present invention.

The carrier is selected from an inorganic carrier or porous hydrophilic carrier. The advantage of inorganic carrier is that the enzyme won't be inactivated and the enzyme adsorbed on the carrier is active, however, the drawback thereof is that the specific activity of enzyme is low, and the amount of adsorbed enzyme per unit of carrier is far below that on porous hydrophilic carrier. The porous hydrophilic carrier can adsorb more enzyme, however, a portion of enzyme will be inactivated, that is, only some of the enzyme adsorbed on the carrier will be active, so that the recovery is low.

The inorganic carrier can be hydrophobic carrier, such as catalyst carrier CELITE [Chemical composition of which is: 87% SiO2, 0.9% CaO, 6.1% $Al_2O_3$, 1.6% Fe2O3, 1.6% Na2O+K2O], expanded perlite [chemical composition of which is: SiO2 (70-75%), CaO (0.1-2.0%), Al2O3 (12-16%), Na2O (1.0-5.0%), Fe2O3 (0.1-1.5%), K2O (1.0-5.0%)], diatomaceous earth, kaolin, or a porous glass, etc., the carriers commonly used in immobilization, and based on the total weight of the inorganic carrier, the SiO2 content is more than 50 wt %, $Al_2O_3$ content is more than 1 wt %; and the inorganic carrier is preferably selected from: catalyst carrier CELITE, expanded perlite, diatomaceous earth, kaolin, or a porous glass; most preferably, catalyst carrier CELITE, expanded perlite.

The porous hydrophilic enzyme carrier can be an enzyme-carrier in which polymethacrylate is used as matrix with bonded epoxide or containing amino functional groups. For example, the enzyme carrier with epoxide as functional group includes Relizyme EP403, SEPABEADS EC-EP. The enzyme carrier with hexylenediamine as functional group includes Relizyme HA403. And The enzyme carrier with hexamethyleneimine as functional group includes SEPABEADS EC-HA.

During the immobilization process by using inorganic carriers, the ratio of enzyme to carrier is 10-100 u of enzyme per gram of carrier; preferably, 20-80 u of enzyme/g of carrier. When the enzyme amount is lower than 10 u/g of carrier, the activity of immobilized enzyme is too low to conducting enzymatic reaction, however, when the enzyme amount is higher than 100 u/g of carrier, the immobilization efficiency of enzyme is too low, so that some of enzyme is in free state and the enzyme activity will lost upon using for one time.

During the immobilization process by using porous hydrophilic carrier, the ratio of enzyme to carrier is 100-1000 u of enzyme per gram of carrier; preferably, 120-600 u of enzyme/g of carrier. In particular, during the immobilization process by using porous hydrophilic carriers, the enzyme liquid is preferably purified, and the lower content of impurity protein in the enzyme liquid will facilitate immobilization.

Immobilization conditions for using inorganic carrier are: the activity of cycloaliphatic peptide acyltransferase in the crude enzyme liquid obtained as above is tested by HPLC; carriers in solid state are added based on certain ratio of enzyme/carrier; at 0-80° C., the resulting system is agitated at pH 4-9 over 0.5 hour; the system is thoroughly washed, filtered, and dried at low temperature, so as to obtain immobilized cycloaliphatic peptide acyltransferase and then stored at 0-5° C.

Immobilization conditions for using porous hydrophilic carrier with epoxide as functional group are: the activity of cycloaliphatic peptide acyltransferase in the purified enzyme liquid obtained as above is tested by HPLC; enzyme carriers with epoxide as functional group are added based on certain ratio of enzyme/carrier; at 0-80° C., the resulting system is agitated at pH 4-9 over 24 hours; the system is thoroughly washed, filtered, and dried at low temperature, so as to obtain immobilized cycloaliphatic peptide acyltransferase and then stored at 0-5° C.

Immobilization conditions for using porous hydrophilic carrier with amino as functional group are: enzyme carriers are pre-activated with glutaraldehyde; upon activation, the carriers are thoroughly washed to remove residual glutaraldehyde; the activity of cycloaliphatic peptide acyltransferase in the purified enzyme liquid obtained as above is tested by HPLC; the enzyme carriers pre-activated with glutaraldehyde are added based on certain ratio of enzyme/carrier; at 0-80° C., the resulting system is agitated at pH 4-9 over 24 hours; the system is thoroughly washed, filtered, and dried at low temperature, so as to obtain immobilized cycloaliphatic peptide acyltransferase and then stored at 0-5° C.

In the present invention, the unit of enzyme activity as said above is defined as: at 40° C., the amount of enzyme for producing 1 μmol of product in 1 hour is defined as 1 u. Steps for testing the enzyme activity are: 17.5 ml of crude enzyme liquid, 5 ml of potassium dihydrogen phosphate buffer (0.25 mol/L, pH 6.0) containing FR901379 and 2.5 ml of methanol are taken respectively; reaction is conducted in a water-bath at 40° C. for 1 hour; the reaction system is suitably diluted with deionized water, filtered with nylon membrane (0.22 um); the concentration of product is tested by HPLC.

Alternatively, in the present invention, the unit of enzyme activity as said above is defined as: at 40° C., the amount of enzyme for producing 1 μmol of product in 1 hour is defined as 1 u. Steps for testing the enzyme activity are: 17.5 ml of crude enzyme liquid, 2.5 ml of solution of echinocandin B in DMSO (100 mg/ml) are taken respectively; 5.0 ml of KCl (1.2 M) and $KH_2PO_4$—$Na_2HPO_4$ buffer (0.5 M) is added into the mixture of the crude enzyme-containing solution and DMSO solution; reaction is conducted in a water-bath at 40° C. for 1 hour; the reaction system is suitably diluted with methanol, filtered with nylon membrane (0.22 um); the concentration of product is tested by HPLC.

In a preferred embodiment of the present invention, the preparation of cycloaliphatic peptide acyltransferase in step a includes the following steps: culturing the strain, and then breaking the cell wall of obtained hyphae, so as to obtain the cycloaliphatic peptide acyltransferase liquid.

The strain refers to an excellent strain capable of secreting cycloaliphatic peptide acyltransferase belonging to *Actinomyces* or *Streptomyces*, mainly including *Actinoplanes utahensis* IFO-13244, *A. utahensis* NRRL-12052. In WO97/32975, enzymes produced by bacteria belonging to *Streptomyces* (*Streptomyces anulatus* 4811 strain, *Streptomyces anulatus* 8703 strain, *Streptomyces* sp. 6907 strain) have been reported. Additionally, in WO97/47738, enzymes produced by *Oidiodendron tenuissimum* IFO 6797 strain, *Oidiodendron echinulatum* IFO 31963 strain, *Oidiodendron truncatum* IFO 9951 strain, *Oidiodendron truncatum* IFO 31812 strain, *Oidiodendron* sp. 30084 strain, *Verticillium* sp. 30085 strain have been reported.

Enzymes produced by *Actinoplanes utahensis* IFO-13244, *A. utahensis* NRRL-12052 and *Streptomyces* sp. 6907 strain are preferred.

The medium for culturing the strain includes the following substances: sucrose 10%, soy peptone 0.1-0.1%, $K_2HPO_4$ 0.1-0.2%, $KH_2PO_4$ 0.01-0.1%, $MgSO_4.7H_2O$ 0.01-0.05%. The strain is cultured at 25-36° C., preferably 30° C., with ventilation being 1-2 vvm, stirring speed being 200-800 r/min. After 3-5 days of culture, great amount of mycelium can be obtained.

The cell wall of mycelium obtained as said above can firstly be broken to collect intracellular enzymes in bacterial cells, so that better cycloaliphatic peptide acyltransferase can be obtained. The cell wall of mycelium can be broken by known methods, such as extraction by high concentration solution of salt, sonication, mechanical crushing, lysozyme method, etc, so that the cycloaliphatic peptide acyltransferase can be transferred out of the cell. And then the enzyme liquid can be separated from mycelium by filtration or centrifugation, so as to obtain a crude enzyme liquid.

For obtaining better immobilized enzymes, the cycloaliphatic peptide acyltransferase liquid can be purified firstly: used inorganic carriers are added into the crude enzyme liquid as obtained above at certain ratio to adsorb free enzymes; the inorganic carriers with adsorbed enzyme are separated from the enzyme liquid; the carriers are thoroughly washed; and the cycloaliphatic peptide acyltransferase is desorbed from the inorganic carriers by using salt solution with high concentration, so as to obtain an enzyme liquid with higher purity.

Ultrafiltration, ion-exchange resin method can be used to purify cycloaliphatic peptide acyltransferase as disclosed in Membrane-associate echinocandin B deacylase of *Actinoplanes utahensis*: purification, characterization, heterologous cloning and enzymatic deacylation reaction. By such method, an enzyme liquid with higher purity can be obtained, however, the recovery of enzyme for this method is low.

In the present invention, deacylation is performed by using immobilized enzymes, comprising the following steps:

A. preparing solution 1 containing cycloaliphatic peptide by adding buffer solution;

B. adding the immobilized cycloaliphatic peptide acyltransferase into solution 1 for conducting deacylation reaction;

C. separating the immobilized cycloaliphatic peptide acyltransferase from the reaction solution containing product.

Wherein the ratio of immobilized cycloaliphatic peptide acyltransferase to cycloaliphatic peptide is 0.01-10 u/g; preferably, 0.1-5 u/g.

In step A, pH of the buffer solution is controlled at 4-9; preferably, 5-7; more preferably, about 6.0. The buffer solution is 0.5 M sodium citrate buffer, 0.5 M $KH_2PO_4$—$Na_2HPO_4$ buffer, Tris-HCl buffer or the mixture thereof; preferably, 0.5 M $KH_2PO_4$—$Na_2HPO_4$ buffer.

In step B, the temperature for deacylation is controlled at about 20-70° C.; preferably, about 30-50° C.

In step C, the method for separating the immobilized enzyme from the reaction solution containing products includes filtration or centrifugation.

After the enzyme is immobilized on suitable carriers, deacylation can be readily conducted in a continuous stirred tank reactor, instead of in batch.

In the present invention, said "cyclic lipopeptide compound" or "cycloaliphatic peptide" refers to a substance of ring-containing peptide, wherein the side chain of the ring contains "acylamino", while other side chains can be contained in such substance.

Representative for such cyclic lipopeptide compound is FR901379 or echinocandin B, which is known as possessing antifungal activities.

The immobilized cycloaliphatic peptide acyltransferase of the invention can deacylate "amide group" on side chain of cycloaliphatic peptide to form "amino group". In particular, the enzyme can deacylate palmitoyl side chain of FR901379 or a salt thereof or acyl side chain of the compound of formula I, so as to form a cyclic peptide of formula II.

As used herein, "pharmaceutically acceptable salt" preferably includes: metal salt such as alkali metal salts (such as sodium salt, potassium salt), alkaline earth metal salt (such as calcium salt, magnesium salt, etc.), ammonium salt, salt formed with organic bases (e.g., trimethylamine salt, triethylamine salt, pyridine salt, picoline salt, dicyclohexylamine salt, N,N,-dibenzylethylenediamine salt, diisopropylethylamine salt, etc.), etc., an organic acid addition salt (e.g. formate, acetate, trifluoroacetate, maleate, tartrate, methanesulfonate, benzenesulfonate, toluenesulfonate, etc.), an inorganic acid addition salt (such as hydrochloride, hydrobromide, hydroiodide, sulfate, phosphate, etc.), salt formed with an amino acid (e.g. arginine, aspartic acid, glutamic acid, etc.), and the like.

The features of the present invention mentioned above, or the features mentioned in the examples, can be optionally combined. Any feature disclosed in the present specification can be used in combination with any other features, and each feature disclosed in the specification can be replaced with alternative feature which can serve an identical, equivalent, or similar purpose. Therefore, the features disclosed herein are only general exemplary examples of the equivalent or similar features, unless specifically indicated otherwise.

The advantages of the invention mainly include:

1. According to the immobilization method for cycloaliphatic peptide acyltransferase provided in the present invention, the enzyme can be repeatedly used, thereby improving the utilization rate of cycloaliphatic peptide acyltransferase, reducing production cost and facilitating industrial production.

2. The purity of the deacylated product of the present invention is significantly improved.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

HPLC detection method for Compound II in the following Examples are described as follows:

Samples are analyzed on Waters analytical HPLC system. Reverse-phase HPLC analysis is used to determine FR179642, Echinocandin B nuclear materials and the like. PLATISIL ODS column (particle size 5 μm, 4.6 mm i.d×250 cm) is used for reverse phase analysis, and remained at 30° C. 3% acetonitrile/0.5% sodium dihydrogen phosphate is used as the mobile phase, flow rate is 1 ml/min, and UV detection is performed at 210 nm.

Example 1

Preparation of Acyltransferase a Produced by *Actinoplanes utahensis* IFO-13244 Strain According to the fermentation method in U.S. Pat. No. 5,376,634, *Actinoplanes utahensis* IFO-13244 strain was cultured to obtain culture containing mycelia (150 L). 0.01 M $KH_2PO_4$ buffer was added, pH value was adjusted to 6.0, 1.0 M KCl was added, and the resulting system was agitated at low temperature over 20 hours for extraction. The resulting mixture was filtered through a Büchner funnel to collect filtrate containing acyltransferase (116 L), namely free enzyme liquid (a). The activity of enzyme in the collected filtrate was detected as $2.3 \times 10^5$ u by HPLC.

Example 2

Preparation of Acyltransferase b Produced by *A utahensis* NRRL-12052 Strain

According to the fermentation method in U.S. Pat. No. 4,320,053, *Actinoplanes utahensis* NRRL-12052 strain was cultured to obtain culture containing mycelia (160 L). 0.01 M $KH_2PO_4$ buffer was added, pH value was adjusted to 6.0, 1.0 M KCl was added, and the resulting system was agitated at low temperature over 20 hours for extraction. The resulting mixture was filtered through a Büchner funnel to collect filtrate containing acyltransferase (121 L), namely free enzyme liquid (b). The activity of enzyme in the collected filtrate was detected as $2.1 \times 10^5$ u by HPLC.

Example 3

Preparation of Acyltransferase c Produced by *Streptomyces* sp. 6907 Strain

According to the fermentation method in WO97/32975, *Streptomyces* sp. 6907 strain was cultured to obtain culture containing mycelia (160 L). 0.01 M $KH_2PO_4$ buffer was added, pH value was adjusted to 6.0, 1.0 M KCl was added, and the resulting system was agitated at low temperature over 20 hours for extraction. The resulting mixture was filtered through a Büchner funnel to collect filtrate containing acyltransferase (124 L), namely free enzyme liquid (c). The activity of enzyme in the collected filtrate was detected as $2.9 \times 10^5$ u by HPLC.

Example 4

Purification of Acyltransferase b

According to the method described in Membrane-associate echinocandin B deacylase of *Actinoplanes utahensis*: purification, characterization, heterologous cloning and enzymatic deacylation reaction, the crude enzyme liquid obtained in Example 2 was purified to give pure acyltransferase liquid (3.0 L), namely free enzyme liquid (d). The activity of enzyme in the collected enzyme liquid was detected as $0.5 \times 10^5$ u by HPLC.

Example 5

Immobilization of Acyltransferase on Inorganic Carrier

For immobilization, 50 L of free enzyme liquid (a), (b), (c) was taken respectively, and then 1.5 kg of expanded perlite was added respectively. The resulting system was agitated over 1 hour for adsorption. The immobilized acyltransferase, i.e., immobilized enzyme (i), (ii) and (iii), was collected by filtration and then washed with 0.01 M $KH_2PO_4$ buffer (pH 6.0) for 3 times, and dried at room temperature for several hours. The immobilized enzyme was stored at 4° C. until use.

TABLE 1

Adsorption ratio of expanded perlite as carrier for different free enzyme liquids

| Immobilized enzyme | acyltransferase | source | Adsorption ratio (%) | Residual enzyme activity u/50 L | Specific activity (u/g wet carrier) |
|---|---|---|---|---|---|
| I | Free enzyme liquid (a) | *Actinoplanes utahensis* IFO-13244 strain | 96.1 | 290 | 21 |
| Ii | Free enzyme liquid (b) | *Actinoplanes utahensis* NRRL-12052 strain | 94.3 | 520 | 18 |
| Iii | Free enzyme liquid (c) | *Streptomyces* sp. 6907 strain | 98.0 | 175 | 25 |

Example 6

Immobilization of Acyltransferase on Porous Hydrophilic Enzyme Carrier with Epoxide as Functional Group For immobilization, two portions of 0.8 L of pure acyltransferase liquid (d) prepared in Example 4 were taken respectively, and 59.2 g of KCl and 0.01 mol/L $KH_2PO_4$ buffer (pH 7.0) were added respectively. And then 30 g of Relizyme EP403 and 30 g of SEPABEADS EC-EP were added respectively. The resulting systems were agitated at 25° C. over 24 hour. The immobilized acyltransferase, i.e., immobilized enzyme (iv), (v), was collected by filtration. The immobilized enzyme was washed with 0.01 M $KH_2PO_4$ buffer (pH 7.0) for 3 times, and dried at room temperature for several hours. The immobilized enzyme was stored at 4° C. until use.

TABLE 2

Immobilization of free enzyme liquid on porous hydrophilic enzyme carrier with epoxide

| Immobilized enzyme | Enzyme carrier | Specific activity (u/g wet carrier) | Residual enzyme activity (u/0.8 L) | Recovery rate (%) |
|---|---|---|---|---|
| iv | Relizyme EP403 | 120 | 80 | 27.2 |
| v | SEPABEADS EC-EP | 212 | 50 | 48.2 |

Example 7

Immobilization of Acyltransferase on Porous Hydrophilic Enzyme Carrier with Amino Group as Functional Group For immobilization, the carrier was pre-activated as follows: 8 g of Relizyme HA403 and 8 g of SEPABEADS EC-HA were taken respectively, and 90 ml of 2% glutaraldehyde solution and 0.02 mol/L $K_2HPO_4$ buffer (pH 8.0) were added. The resulting system was agitated at 20-25° C. for 1 hour. Supernatant was removed, and the resins were washed with pure water. Two portions of 0.4 L of pure acyltransferase liquid (d) prepared in Example 4 were taken respectively, and two portions of activated carriers were added respectively. The resulting systems were agitated at 20-25° C. over 20 hour. The immobilized acyltransferase, namely immobilized enzyme (vi), (vii), was collected by filtration. The immobilized enzyme was washed with 0.01 M $KH_2PO_4$ buffer (pH 7.0) for 3 times, and dried at room temperature for several hours. The immobilized enzyme was stored at 4° C. until use.

TABLE 3

Immobilization of free enzyme liquid on porous hydrophilic enzyme carrier of amino type

| Immobilized enzyme | Enzyme carrier | Specific activity (u/g wet carrier) | Residual enzyme activity (u/0.4 L) | Recovery rate (%) |
|---|---|---|---|---|
| (vi) | Relizyme HA403 | 600 | 30 | 72.7 |
| (vii) | SEPABEADS EC-HA | 380 | 10 | 46.0 |

Example 8

Deacylation in Batches by Immobilized Enzyme

2 L of buffer (0.2 M $KH_2PO_4$—$Na_2HPO_4$ buffer; pH 6.0) and 15 g of immobilized enzyme (i), immobilized enzyme (ii), or immobilized enzyme (iii) were added into 2 L of FR901379 aqueous solution (20 mg/ml, HPLC purity of 79.2%; 20 g of FR901379, 16.7 mmol). Deacylation reaction was conducted at 40° C. for 4 hours. The production and purity of FR179642 were detected by HPLC.

TABLE 4

Conversion rate of FR901379 and purity of FR179642 after conducting deacylation for 4 hours by using immobilized enzymes

| Immobilized enzyme | Conversion rate X (%) | Purity of FR179642 (%) |
|---|---|---|
| Immobilized enzyme (i) | 94.6 | 95.2 |
| Immobilized enzyme (ii) | 95.2 | 94.7 |
| Immobilized enzyme (iii) | 98.7 | 95.9 |

Example 9

Deacylation in Batches by Immobilized Enzyme

2 L of buffer (0.2 M $KH_2PO_4$—$Na_2HPO_4$ buffer; pH 6.0) and 15 g of immobilized enzyme (iv), immobilized enzyme (v), immobilized enzyme (vi) or immobilized enzyme (vii) were added into 2 L of FR901379 aqueous solution (20 mg/ml, HPLC purity of 79.2%; 20 g of FR901379, 16.7 mmol). Deacylation reaction was conducted at 40° C. for 1 hour. The production and purity of FR179642 were detected by HPLC.

TABLE 5

Conversion rate of FR901379 and purity of FR179642 after conducting deacylation for 1 hours by using immobilized enzymes

| Immobilized enzyme | Conversion rate X (%) | Purity of FR179642 (%) |
|---|---|---|
| Immobilized enzyme (iv) | 92.1 | 94.8 |
| Immobilized enzyme (v) | 93.7 | 94.7 |
| Immobilized enzyme (vi) | 94.7 | 95.1 |
| Immobilized enzyme (vii) | 94.5 | 94.2 |

Comparative Example 1

Experiment in Batches by Free Enzyme Liquid

According to deacylation method in WO97/32975, 100 ml of buffer (0.2 M $KH_2PO_4$—$Na_2HPO_4$ buffer; pH 6.0) and 100 ml of methanol were added into 100 ml of FR901379 aqueous solution (100 mg/ml, HPLC purity of 79.2%; 10 g of FR901379, 38.35 mmol). And then 700 ml of free enzyme liquid (c) was added. Deacylation reaction was conducted at 40° C. for 7 hours with a conversion rate of 71.1%. The purity of FR17964 was detected as 75.7% by HPLC. HPLC analytical patterns can be found in FIG. 2 and table 10.

Upon conversion, almost no enzyme activity can be detected in the liquid. Almost all of enzyme was inactivated during conversion.

TABLE 10

Figure 2:
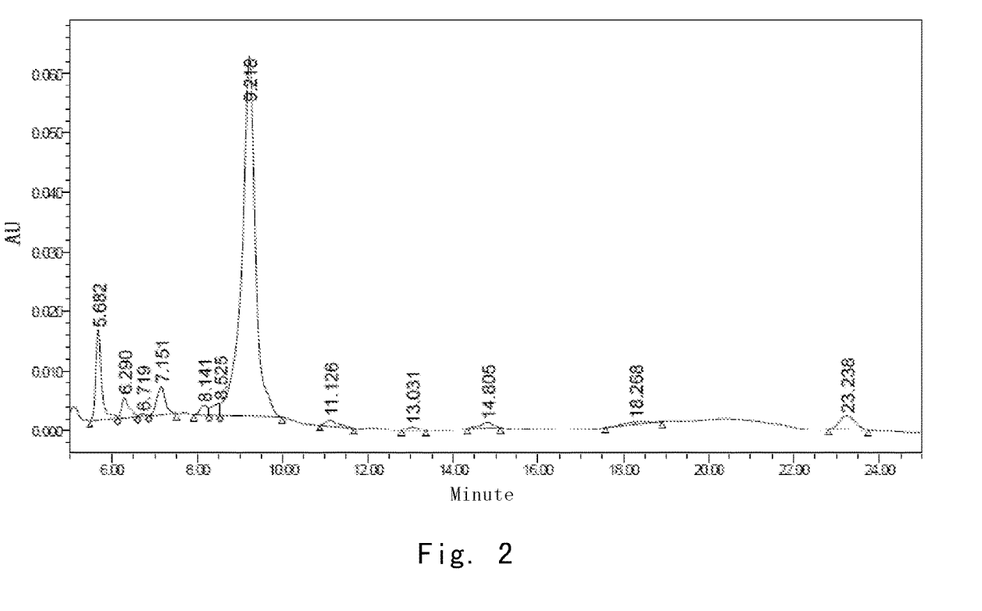
FIG. 2 is HPLC pattern of deacylated product obtained by using the free enzyme liquid in Comparative Example 1.

| Peak No. | Retention time (Min) | Peak Area (mV * s) | Peak Height (mV) | % Area |
|---|---|---|---|---|
| 1 | 5.682 | 142308 | 14951 | 8.09 |
| 2 | 6.290 | 40524 | 3337 | 2.30 |
| 3 | 6.719 | 4818 | 463 | 0.27 |
| 4 | 7.151 | 65642 | 4673 | 3.73 |
| 5 | 8.141 | 20293 | 1597 | 1.15 |
| 6 | 8.525 | 25462 | 2034 | 1.45 |
| 7 | 9.218 | 1332042 | 60431 | 75.72 |
| 8 | 11.126 | 21882 | 1041 | 1.24 |
| 9 | 13.031 | 8234 | 516 | 0.47 |
| 10 | 14.805 | 20289 | 961 | 1.15 |
| 11 | 18.268 | 16222 | 421 | 0.92 |
| 12 | 23.238 | 61491 | 2382 | 3.50 |

It can be seen from the above Examples and Comparative Example 1 that, compared with deacylation using free enzyme liquid, deacylation using immobilized enzyme possesses significant advantages. The conversion rate and purity of product have been greatly improved.

Example 10

Continuous Deacylation in Continuous Stirred Tank Reactor

At 45° C., continuous deacylation from FR901379 to FR179642 was performed in a 50 L continuous stirred tank reactor. 0.3 Kg of immobilized enzyme (vi), 20 L of FR901379 aqueous solution (20 mg/ml, HPLC purity of 79.2%), and 20 L of buffer (0.2 M $KH_2PO_4$—$Na_2HPO_4$ buffer; pH 6.0) were added. After 3 hours, the conversion rate of substrate achieved 95.99%. HPLC analytical patterns can be found in FIG. 1 and table 6.

TABLE 6

Figure 1:
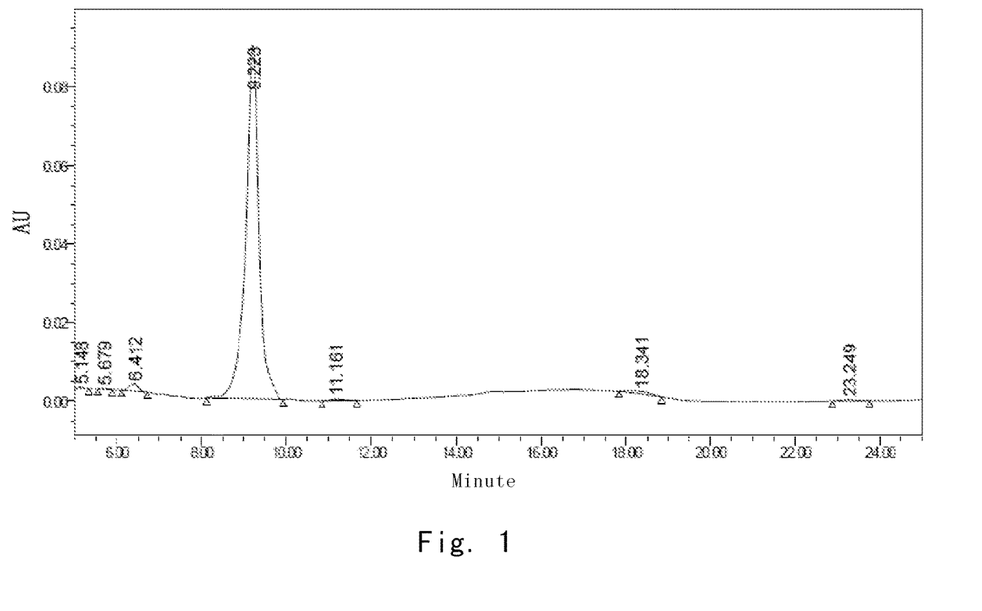
FIG. 1 is HPLC pattern of deacylated product obtained by using the immobilized enzyme (vi) in Example 10.

| Peak No. | Retension time (Min) | Peak Area (mV * s) | Peak Height (mV) | % Area |
|---|---|---|---|---|
| 1 | 5.148 | 6472 | 590 | 0.32 |
| 2 | 5.679 | 3661 | 467 | 0.18 |
| 3 | 6.412 | 29895 | 2111 | 1.48 |
| 4 | 9.223 | 1940814 | 90329 | 95.99 |
| 5 | 11.161 | 8269 | 386 | 0.41 |
| 6 | 18.341 | 24274 | 694 | 1.20 |
| 7 | 23.249 | 8466 | 334 | 0.42 |

The immobilized acyltransferase can remain stable and active for at least 30 hours, therefore, it can be used for more than 5 times during production.

Compared with Comparative Example 1, it can be seen from Example 10 that immobilized enzyme can be repeatedly used, so that the usage rate can be greatly improved and the damage and pollution to environment can be reduced.

Example 11

Comparison of Immobilization Between Different Carriers for Free Enzyme and of Deacylation Between Immobilized Enzymes For immobilization, 5 L of free enzyme (c) was taken, and then 0.15 kg of expanded perlite, CELITE, active carbon ($SiO_2$ content is lower than 0%), molecular sieve, and porous glass were added respectively. The resulting systems were agitated at 30° C. over 1 hour. The immobilized acyltransferase, namely immobilized enzyme (viii), (ix), (x), (xi), (xii), was collected by filtration. The immobilized enzyme was washed with 0.01 M $KH_2PO_4$ buffer (pH 6.0) for 3 times, and dried at room temperature for several hours. The immobilized enzyme was stored at 4° C. until use.

Then, 2 L of buffer (0.2 M $KH_2PO_4$—$Na_2HPO_4$ buffer; pH 6.0) and 15 g of immobilized enzyme (viii), (ix), (x), (xi), (xii) were added into 2 L of FR901379 aqueous solution (20 mg/ml, HPLC purity of 79.2%; 20 g of FR901379, 16.7 mmol) respectively. Deacylation reaction was conducted at 40° C. for 4 hours. The production and purity of FR179642 were detected by HPLC.

TABLE 7

Comparison of adsorption rate between 3 carriers for free enzyme and of deacylation between immobilized enzymes

| Carrier | Adsorption rate (%) | Conversion rate X (%) | Purity of FR179642 (%) |
|---|---|---|---|
| Expanded perlite (viii) | 98.0 | 98.7 | 94.9 |
| CELITE (ix) | 99.1 | 95.2 | 95.8 |
| Active carbon (x) | 2.6 | 1.2 | |
| Molecular sieve (xi) | 0.5 | 0.1 | |
| Porous glass (xii) | 1.0 | 0.2 | |

Example 12

Comparison of Carriers Under Different Ratios for Immobilization Between Free Enzyme and of Deacylation Between Immobilized Enzymes For immobilization, 7 portions of 5 L of free enzyme liquid (c) were taken, the enzyme activity of which was detected as $1.17 \times 10^4$ U by HPLC. And then, 0.05 kg, 0.12 kg, 0.15 kg, 0.24 kg, 0.58 kg, 1.17 kg, and 1.75 kg, of CELITE were added respectively. The resulting systems were agitated at 30° C. over 1 hour for adsorption. The immobilized acyltransferase was collected by filtration. The immobilized enzyme was washed with 0.01 M $KH_2PO_4$ buffer (pH 6.0) for 3 times, and the enzyme activity in filtrate was detected by HPLC. The immobilized enzyme was dried at room temperature for several hours, and stored at 4° C. until use.

Then, 1 L of buffer (0.2 M $KH_2PO_4$—$Na_2HPO_4$ buffer; pH 6.0) and 75 g of immobilized enzymes as above prepared were added into 1 L of FR901379 aqueous solution (20 mg/ml, HPLC purity of 79.2%; 10 g of FR901379, 8.35 mmol) respectively. Deacylation reaction was conducted at 40° C. for 4 hours. The production and purity of FR179642 were detected by HPLC.

TABLE 8

Comparison of adsorption rate between carriers for free enzyme under different ratios and of deacylation between immobilized enzymes

| Ratio of enzyme to carrier (U/g) | Adsorption rate (%) | Conversion rate X (%) |
|---|---|---|
| 243/1 | 46.1 | 60.3 |
| 97.5/1 | 82.0 | 99.1 |
| About 80.0/1 | 98.1 | 97.2 |
| About 50.0/1 | 98.5 | 95.7 |
| 20.0/1 | 99.5 | 93.9 |
| 10/1 | 98.2 | 87.8 |
| 15/1 | 98.1 | 41.2 |

Example 13

Comparison of Immobilization of Carriers for Free Enzyme Under Different pH

For immobilization, 5 portions of 5 L of free enzyme liquid (a) were taken, the enzyme activity of which was detected as $1.0 \times 10^4$ U by HPLC. And then, 0.15 kg of CELITE was added respectively. pH was adjusted to 3.5, 4.0, 6.0, 9.0, 9.5 by using 2 mol/l HCl or 2 mol/l NaOH respectively. The resulting systems were agitated at 25° C. over 1 hour for adsorption. The immobilized acyltransferase was collected by filtration. The immobilized enzyme was dried at room temperature for several hours, and stored at 4° C. until use.

Then, 1 L of buffer (0.2 M $KH_2PO_4$—$Na_2HPO_4$ buffer; pH 6.0) and 75 g of immobilized enzymes as above prepared were added into 1 L of FR901379 aqueous solution (20 mg/ml, HPLC purity of 79.2%; 10 g of FR901379, 8.35 mmol) respectively. Deacylation reaction was conducted at 40° C. for 4 hours. The production of FR179642 was detected by HPLC.

TABLE 9

Comparison of immobilization of carriers for free enzyme under different pH

| Immobilization pH | Conversion rate X (%) |
|---|---|
| 3.5 | 8.6 |
| 4.0 | 89.1 |
| 6.0 | 96.2 |
| 9.0 | 95.9 |
| 9.5 | 61.5 |

Example 14

500 ml of KCl (1.2 M) and $KH_2PO_4$—$Na_2HPO_4$ buffer (0.5 M, pH 7.0) was added into 100 mL of echinocandin B solution in DMSO (100 mg/ml, 10 g of Echinocandin B, 9.43 mmol). And then 25 g of immobilized enzyme (ii) was added. Deacylation reaction was conducted at 50° C. for 2 hours. The conversion rate was detected 85.6%.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:

1. A method for preparing a compound of formula II, comprising:
   (a) mixing the compound of formula I with a buffer solution, so as to obtain a solution 1; and
   (b) mixing the solution 1 with an immobilized cycloaliphatic peptide acyltransferase derived from Actinoplanes utahensis IFO-13244 strain for conducting a deacylation reaction, so as to produce the compound of formula II in a product-containing reaction solution comprising the compound of formula II,

I

II wherein $R^1$ is acyl, $R^2$ is hydroxy or acyloxy, $R^3$ is hydrogen or hydroxy, $R^4$ is hydrogen or hydroxy, $R^5$ is hydrogen or hydroxy sulfonyloxy, and $R^6$ is hydrogen or carbamoyl;

the immobilized cycloaliphatic peptide acyltransferase is obtained by immobilizing the cycloaliphatic peptide acyltransferase derived from Actinoplanes utahensis IFO-13244 strain onto an expanded perlite, which is a chemical composition that contains 70-75% $SiO_2$, 0.1-2.0% $CaO$, 12-16% $Al_2O_3$, 1.0-5.0% $Na_2O$, 0.1-1.5% $Fe_2O_3$, and 1.0-5.0% $K_2O$ at pH 6-9, wherein the immobilized cycloaliphatic peptide acyltransferase catalyzes the deacylation of $R^1$ of the compound of formula I which results in the formation of the compound of formula II, wherein the compound of formula I is the compound of formula Ia or Ib or a pharmaceutically acceptable salt thereof:

2. The method according to claim 1, wherein the ratio of the immobilized cycloaliphatic peptide acyltransferase to the compound of formula I is 0.01-10 u/g.

3. The method according to claim 1, wherein the pH value of the buffer solution in (a) is 4-9.

4. The method according to claim 1, wherein the buffer solution in (a) is selected from the group consisting of sodium citrate buffer, potassium dihydrogen phosphate-disodium hydrogen phosphate buffer and Tris-HCl buffer.

5. The method according to claim 1, wherein the temperature for the deacylation reaction in (b) is 20-70° C.

6. The method according to claim 1, further comprising after (b), separating the immobilized cycloaliphatic peptide acyltransferase from the product-containing reaction solution to obtain the compound of formula II.

7. The method according to claim 6, wherein the separating is carried out by filtration or centrifugation.

8. The method according to claim 1, wherein the conversion rate of the compound of formula Ia by the cycloaliphatic peptide acyltransferase derived from Actinoplanes utahensis IFO-13244 strain immobilized on expanded perlite to yield the compound of formula Ic:

is 94.6% at 4 hours in $KH_2$—$Na_2HPO_4$ buffer at pH 6 and 40° C.

* * * * *